United States Patent
Kimura et al.

(10) Patent No.: US 10,064,585 B2
(45) Date of Patent: Sep. 4, 2018

(54) PHOTON DETECTING ELEMENT, PHOTON DETECTING DEVICE, AND RADIATION ANALYZING DEVICE

(71) Applicant: KABUSHIKI KAISHA TOSHIBA, Tokyo (JP)

(72) Inventors: Shunsuke Kimura, Kanagawa (JP); Hiroshi Ota, Saitama (JP); Go Kawata, Kanagawa (JP); Hideyuki Funaki, Tokyo (JP); Rei Hasegawa, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 435 days.

(21) Appl. No.: 14/849,049

(22) Filed: Sep. 9, 2015

(65) Prior Publication Data

US 2016/0084964 A1 Mar. 24, 2016

(30) Foreign Application Priority Data

Sep. 19, 2014 (JP) .................................. 2014-191577

(51) Int. Cl.
*H01L 27/146* (2006.01)
*A61B 6/03* (2006.01)
*A61B 6/00* (2006.01)
*G01T 1/24* (2006.01)

(52) U.S. Cl.
CPC ............ *A61B 6/032* (2013.01); *A61B 6/4241* (2013.01); *G01T 1/248* (2013.01); *A61B 6/4035* (2013.01)

(58) Field of Classification Search
CPC ....... H01L 31/02027; G05F 3/18; H03G 3/24; H03G 1/0047; H01J 40/14; G01R 19/0092

See application file for complete search history.

(56) References Cited

U.S. PATENT DOCUMENTS

| | | | | |
|---|---|---|---|---|
| 3,953,807 A | * | 4/1976 | Schade, Jr. ............. | G05F 3/262 330/277 |
| 4,292,514 A | * | 9/1981 | Ohtomo ............ | H01L 31/02027 250/214 C |
| 5,548,112 A | | 8/1996 | Nakase et al. | |
| 5,578,815 A | * | 11/1996 | Nakase ..................... | G05F 3/18 250/214 C |

(Continued)

FOREIGN PATENT DOCUMENTS

| | | |
|---|---|---|
| JP | 54-121087 | 9/1979 |
| JP | 7-27607 | 1/1995 |

(Continued)

*Primary Examiner* — Kiho Kim

(74) *Attorney, Agent, or Firm* — Finnegan, Henderson, Farabow, Garrett & Dunner, L.L.P.

(57) ABSTRACT

According to an embodiment, a photon detecting element includes one or more avalanche photodiodes and a circuit. The circuit is connected between cathodes of the one or more avalanche photodiodes and an external power source. The circuit is configured in which a first temperature coefficient representing variation of a setting potential with respect to temperature variation when constant-current driving is performed so that electrical potential of the cathodes becomes equal to the setting potential is substantially the same as a second temperature coefficient representing variation of breakdown voltage of the one or more avalanche photodiodes with respect to temperature variation.

6 Claims, 8 Drawing Sheets

(56) References Cited

U.S. PATENT DOCUMENTS

| | | | | |
|---|---|---|---|---|
| 5,929,982 A * | 7/1999 | Anderson | ................ | H03G 3/24 |
| | | | | 250/214 AG |
| 8,901,475 B1 * | 12/2014 | Joffe | ........................ | H03F 3/087 |
| | | | | 250/214 A |
| 2006/0027736 A1 * | 2/2006 | Ichino | ............... | H01L 31/02027 |
| | | | | 250/214 R |
| 2009/0267589 A1 * | 10/2009 | Zhang | ................ | G01R 19/0092 |
| | | | | 324/123 R |
| 2012/0246295 A1 | 10/2012 | Ito et al. | | |

FOREIGN PATENT DOCUMENTS

| | | |
|---|---|---|
| JP | 07-176782 | 7/1995 |
| JP | 2000-252507 | 9/2000 |
| JP | 2002-084235 | 3/2002 |
| JP | 2011-7693 | 1/2011 |
| JP | 2011-204879 | 10/2011 |
| JP | 2013-195254 | 9/2013 |

\* cited by examiner

PHOTON DETECTING ELEMENT, PHOTON DETECTING DEVICE, AND RADIATION ANALYZING DEVICE

CROSS-REFERENCE TO RELATED APPLICATION

This application is based upon and claims the benefit of priority from Japanese Patent Application No. 2014-191577, filed on Sep. 19, 2014; the entire contents of which are incorporated herein by reference.

FIELD

An embodiment described herein relates generally to a photon detecting element, a photon detecting device, and a radiation analyzing device.

BACKGROUND

During radiation detection performed according to the photon counting method used at a high count rate in medical applications, in order to accurately obtain the energy of radiation photons, the photoelectric conversion gain of an avalanche photodiode (APD) for photon detection, which detects radiation photons, needs to be maintained at a constant level while performing the measurement.

An APD has a voltage higher than the breakdown voltage applied in between the anode and the cathode, and operates in a Geiger mode. The photoelectric conversion gain of an APD is proportional to the voltage applied excessively (the excessive voltage) against the breakdown voltage. On the other hand, the breakdown voltage varies according to the temperature. Hence, since the excessive voltage varies in response to a change in the surrounding temperature, the photoelectric conversion gain of the APD also varies. Thus, in order to perform measurement while keeping the photoelectric conversion gain of the APD at a constant level, it is necessary to keep a constant excessive voltage applied to the APD regardless of the temperature variation.

Meanwhile, a type of feedback control is known in which the surrounding temperature of an APD is detected using a temperature sensor, and the power-supply voltage of the APD is controlled according to the temperature variation using peripheral circuitry including a central processing unit (CPU).

However, in order to vary the inverse voltage which is applied to an APD according to the temperature, it is necessary to install a temperature sensor, a temperature sensor driving circuit, and a bias voltage varying circuit. Hence, the configuration becomes complex and the processing time also becomes long.

DETAILED DESCRIPTION

According to an embodiment, a photon detecting element includes one or more avalanche photodiodes and a circuit. The circuit is connected between cathodes of the one or more avalanche photodiodes and an external power source. The circuit is configured in which a first temperature coefficient representing variation of a setting potential with respect to temperature variation when constant-current driving is performed so that electrical potential of the cathodes becomes equal to the setting potential is substantially the same as a second temperature coefficient representing variation of breakdown voltage of the one or more avalanche photodiodes with respect to temperature variation.

An exemplary embodiment of a photon detecting device 100 is described below with reference to the accompanying drawings.

Figure 1:
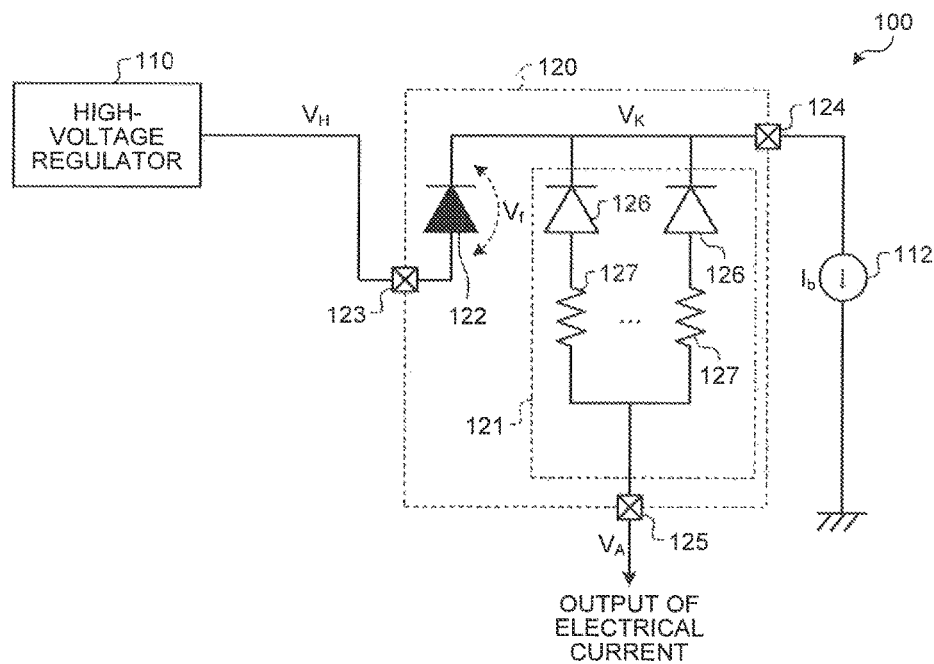
FIG. 1 is a configuration diagram that schematically illustrates a configuration of a photon detecting device according to an embodiment.

FIG. 1 is a configuration diagram that schematically illustrates a configuration of the photon detecting device 100 according to the embodiment. For example, the photon detecting device 100 includes a high-voltage regulator (a power supply) 110, a current sink circuit 112, and a photon detecting element 120.

The high-voltage regulator 110 applies such a voltage to the photon detecting element 120 that the photon detecting element 120 operates in a Geiger mode in which the inverse voltage is set to be equal to or greater than the breakdown voltage. The current sink circuit 112 draws in such an electrical current that the high-voltage regulator 110 performs constant-current driving of a nonlinear circuit (such as a diode 122) (described later) of the photon detecting element 120. Herein, the current sink circuit 112 can be a resistance.

The photon detecting element 120 includes a pixel 121, which detects photons, and the diode (nonlinear circuit) 122. Moreover, the photon detecting element 120 has the following components disposed thereon: a terminal 123 to which an output voltage $V_H$ is applied from the high-voltage regulator 110; a terminal 124 that outputs an electrical current to the current sink circuit 112; and a terminal 125 that outputs an electrical current corresponding to the photons detected by the pixel 121.

Meanwhile, in FIG. 1, the photon detecting element 120 is illustrated to have a single pixel 121 and a single diode 122. Alternatively, as described later with reference to FIG. 7, for example, the photon detecting element 120 is configured with a plurality of pixels and a plurality of diodes. Still alternatively, the diode 122 can be included in the pixel 121.

The pixel 121 includes, for example, a plurality of avalanche photodiodes (APDs) 126 and a plurality of quenching resistances 127. The pixel 121 superimposes pulses, each of which represents the charge amount output by one of the APDs 126 having photons incident thereon via the corresponding quenching resistance 127; and outputs the superimposed pulses from the terminal 125. That is, according to the photon count detected on a pixel-by-pixel basis, the photon detecting element 120 outputs an electrical current.

A cathodic potential $V_K$ of the APDs 126 is determined as given below in Equation (1) according to the output voltage $V_H$ of the high-voltage regulator 110 and a forward voltage $V_f$ of the diode 122.

$$V_K = V_H - V_f \qquad (1)$$

Thus, the diode 122 is connected in between the cathodes of the APDs 126 and the high-voltage regulator 110, and is used as a diode for cathodic potential control with respect to the APDs 126. Herein, the terminal 125 (the anodic side of the APDs 126) is applied with such a voltage that a predetermined electrical potential $V_A$ is achieved.

As given below in Equation (2), the forward voltage $V_f$ of the diode 122 is determined according to a sink current $I_b$ that is drawn in by the current sink circuit 112 operating as a constant current source.

$$V_f = T \times (k/q) \times \log(I_b/I_0 + 1) \qquad (2)$$

where T represents the temperature of the diode, k represents the Boltzmann constant, q represents the elementary charge, $I_0$ represents the dark current determined according to the concentration profile of the diode.

In Equation (2), if the constant terms other than the temperature T are set to "a", then the forward voltage $V_f$ is represented as Equation (3) given below that includes a temperature coefficient a.

$$V_f = a \times T \qquad (3)$$

As given below in Equation (4), a breakdown voltage $V_{br}$ for the APDs 126 is determined according to the temperature T of the diode, a breakdown voltage $V_0$ at a temperature 0K, and a temperature coefficient b.

$$V_{br} = V_0 + b \times T \qquad (4)$$

An excessive voltage $V_{ov}$ that is applied to the APDs 126 in excess of the breakdown voltage is represented in Equation (5) given below.

$$V_{ov} = (V_K - V_A) - V_{br} = (V_H - a \times T) - V_A - (V_0 + b \times T) \qquad (5)$$

Meanwhile, if the temperature changes from an initial temperature T1 to a temperature T2, an amount of variation $\Delta V_{ov}$ in the excessive voltage with respect to the temperature is given below in Equation (6).

$$\Delta V_{ov} = ((V_H - a \times T1) - V_A - (V_0 + b \times T1)) - \qquad (6)$$
$$((V_H - a \times T2) - V_A - (V_0 + b \times T2)) =$$
$$-a \times (T1 - T2) + b \times (T1 - T2)$$

Herein, if the temperature coefficient a of the forward voltage $V_f$ of the diode 122 is equal to the temperature coefficient b of the breakdown voltage of the APDs 126, the amount of variation in the excessive voltage due to the temperature variation gets cancelled out. Hence, a constant excessive voltage gets applied on a constant basis between the anode and the cathode of each APD 126. That is, in concert with the temperature coefficient b of the breakdown voltage of the APDs 126, the temperature coefficient a in the forward direction $V_f$ of the diode 122 is made to correspond using the design of the concentration profile. As a result, it becomes possible to enhance the accuracy of cancelling out the amount of variation in the excessive voltage.

Figure 2:
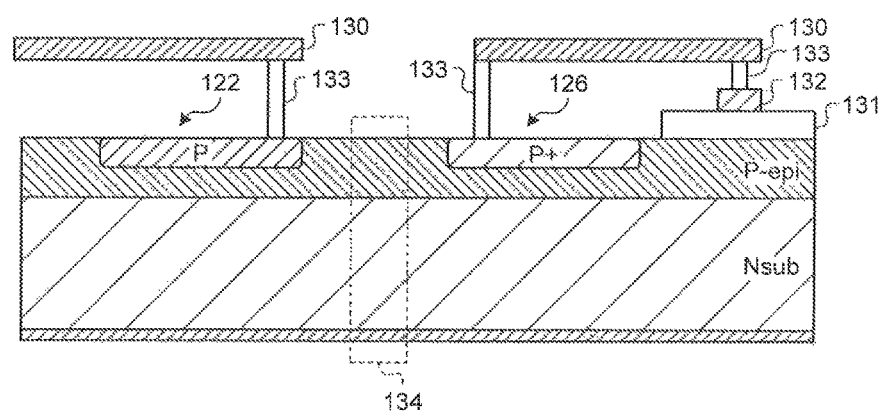
FIG. 2 is a diagram illustrating a specific example of the device structure of an avalanche photodiode (APD) and a diode.

FIG. 2 is a diagram illustrating a specific example of the device structure of the APD 126 and the diode 122. As illustrated in FIG. 2, the APD 126 is connected to a resistance (the quenching resistance 127), which is formed by a polysilicon 132 laminated on an insulator layer 131, by a contact 133 via hard-wiring (first hard-wiring layer) 130. The APD 126 and the diode 122 are separated by element isolation 134. The diode 122 is configured in the lamination direction and is connected to the hard-wiring 130 by the contact 133.

Figure 3:
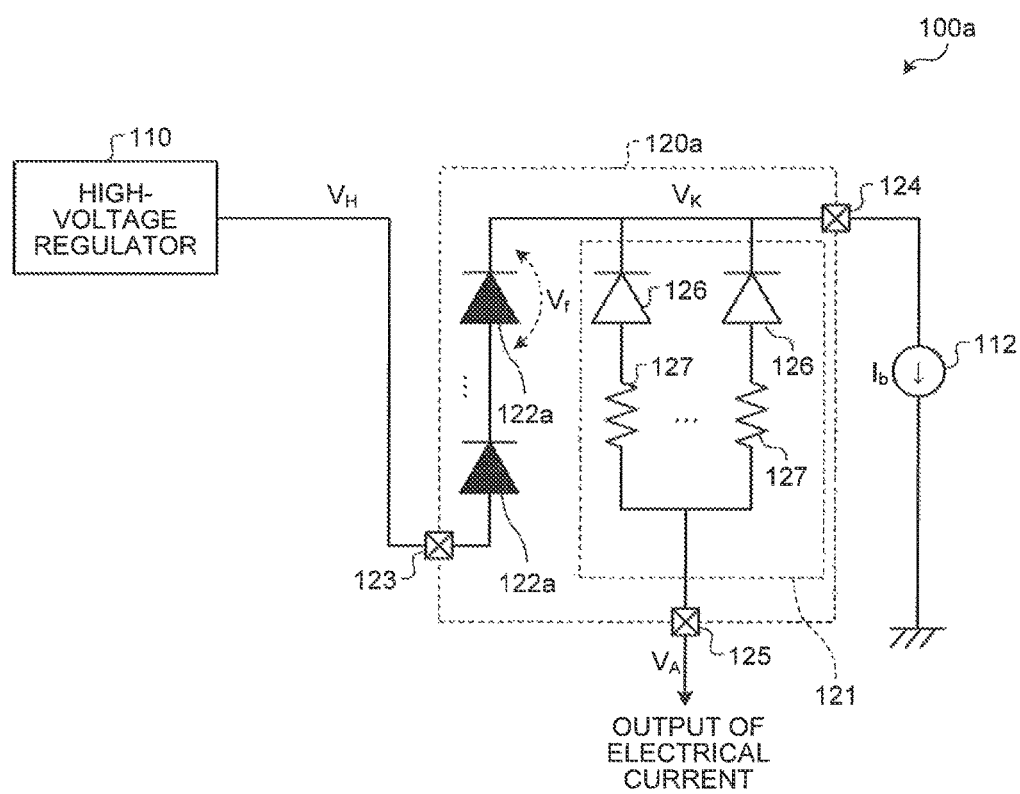
FIG. 3 is a diagram illustrating a first modification example of the photon detecting device according to the device.

FIG. 3 is a diagram illustrating a first modification example of the photon detecting device 100 (illustrating a photon detecting device 100a). As illustrated in FIG. 3, the photon detecting device 100a includes, for example, the high-voltage regulator 110, the current sink circuit 112, and a photon detecting element 120a. Meanwhile, of the constituent elements of the photon detecting device 100a illustrated in FIG. 3, the constituent elements that are substantially identical to the constituent elements of the photon detecting device 100 (FIG. 1) are referred to by the same reference numerals.

The photon detecting element 120a includes the pixel 121 and a plurality of diodes (nonlinear circuits) 122a that are connected in series. In the photon detecting element 120a, the cathodic potential $V_K$ of the APDs 126 is determined as given below in Equation (7) according to the output voltage $V_H$ of the high-voltage regulator 110 and the forward voltage $V_f$ the diodes 122a connected in series.

$$V_K = V_H - n \times V_f \qquad (7)$$

Herein, n represents the number of diodes 122a connected in series. The forward voltage $V_f$ of each diode 122a is determined according to the sink current $I_b$ drawn in by the current sink circuit 112 operating as a constant current source.

Meanwhile, if the temperature changes from the initial temperature T1 to the temperature T2, the amount of variation $\Delta V_{ov}$ in the excessive voltage with respect to the temperature is given below in Equation (8).

$$\Delta V_{ov} = ((V_R - n \times a \times T1) - V_A - (V_0 + b \times T1)) - \qquad (8)$$
$$((V_H - n \times a \times T2) - V_A - (V_0 + b \times T2)) =$$
$$-a \times (T1 - T2) + b \times (T1 - T2)$$

If the product of the temperature coefficient a of the forward voltage $V_f$ of the diodes 122a and the number n of diodes 122a is equal to the temperature coefficient b of the breakdown voltage of the APDs 126, then the amount of variation in the excessive voltage attributed to the temperature variation gets cancelled out. For that reason, a constant excessive voltage gets applied on a constant basis between the anode and the cathode of each APD 126. That is, if the number n of diodes 122a is set in concert with the temperature coefficient b of the breakdown voltage of the APDs 126, it becomes possible to enhance the accuracy of cancelling out the amount of variation in the excessive voltage.

Figure 4:
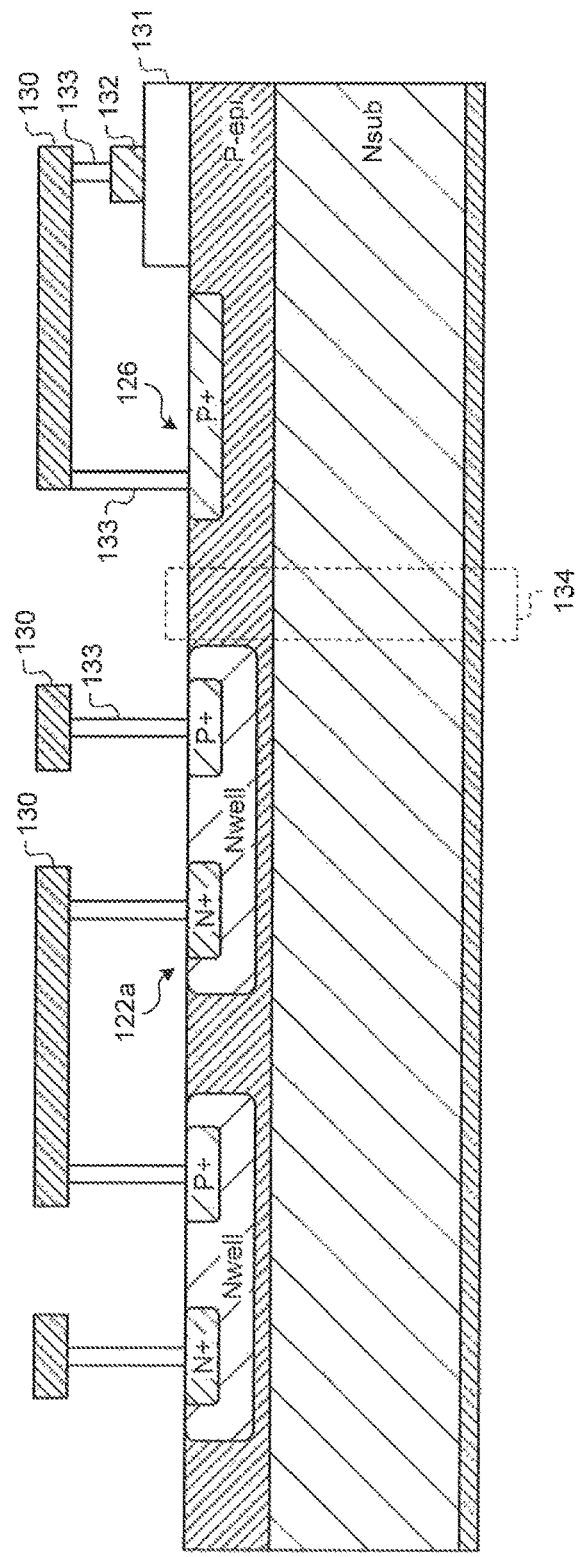
FIG. 4 is a diagram illustrating a specific example of the device structure of an APD and diodes.

FIG. 4 is a diagram illustrating a specific example of the device structure of the APD 126 and the diodes 122a. Of the constituent elements illustrated in FIG. 4, the constituent elements that are substantially identical to the constituent elements illustrated in FIG. 2 are referred to by the same reference numerals. As illustrated in FIG. 4, each diode 122a is connected to the hard-wiring 130 by the contact 133. With that, the diodes 122a get connected m series.

Figure 5:
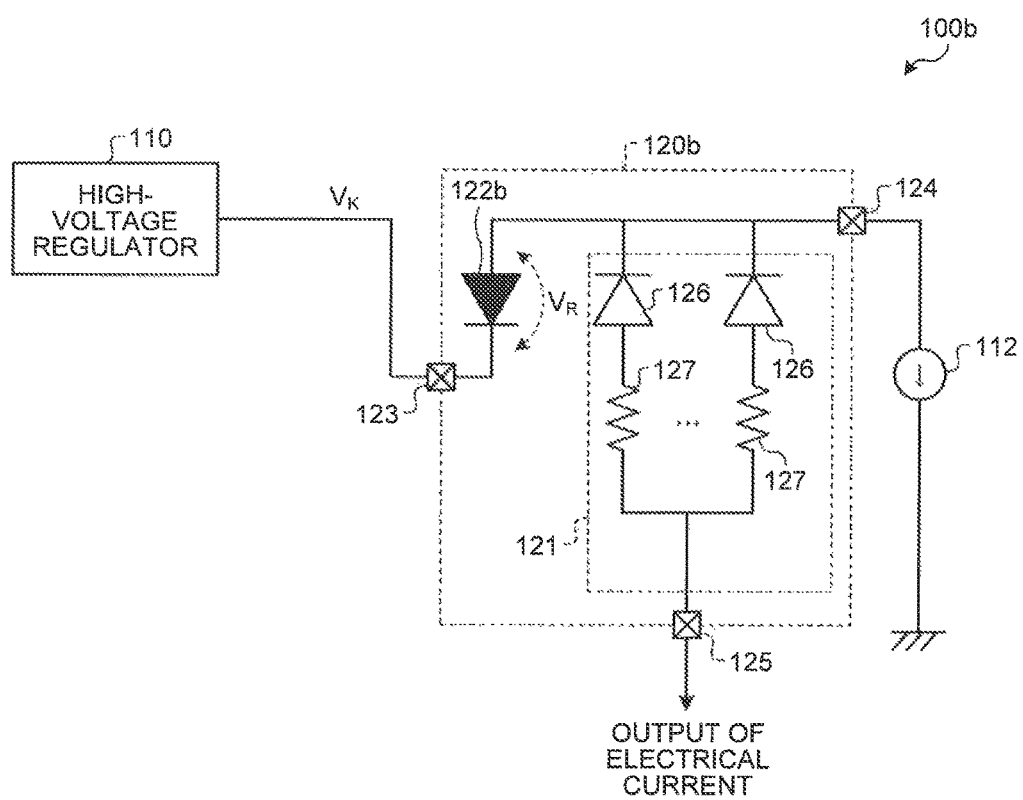
FIG. 5 is a diagram illustrating a second modification example of the photon detecting device according to the device.

FIG. 5 is a diagram illustrating a second modification example of the photon detecting device 100 (illustrating a photon detecting device 100b). As illustrated in FIG. 5, the photon detecting device 100b includes, for example, the high-voltage regulator 110, the current sink circuit 112, and a photon detecting element 120b. Meanwhile, of the constituent elements of the photon detecting device 100b illustrated in FIG. 5, the constituent elements that are substantially identical to the constituent elements of the photon detecting device 100 (FIG. 1) are referred to by the same reference numerals.

The photon detecting element 120b includes the pixel 121 and, for example, a single Zener diode (a nonlinear circuit) 122b. The Zener diode 122b has its cathode connected to the anode of each APD 126, and has an inverse voltage $V_R$ applied thereto by the high-voltage regulator 110.

Moreover, with respect to the temperature coefficient (a second temperature coefficient) representing the variation of the breakdown voltage of the APDs 126 with respect to the temperature variation, the temperature coefficient (a first temperature coefficient) representing the variation of the breakdown voltage of the Zener diode 122b with respect to the temperature variation is set to be substantially same. That is, the Zener diode 122b sets the electrical potential of the cathodes of the APDs 126 at a smaller electrical current than the electrical current used by the diode 122 illustrated in FIG. 1. Meanwhile, as far as the substantially same temperature coefficients are concerned, for example, with reference to the value of the second temperature coefficient, the first temperature coefficient is within the range of ±30% of the second temperature coefficient. Moreover, it is desirable that the first temperature coefficient is within the range of ±10% of the second temperature coefficient. Of course, in the photon detecting element 120, if the first temperature coefficient does not lie with the abovementioned range, as long as the temperature characteristic of the multiplication factor of the APDs 126 is compensated, the condition is allowed. For example, in the photon detecting element 120b, the first temperature coefficient can be set in an arbitrary manner according to the usage environment and the acceptable error.

Figure 6:
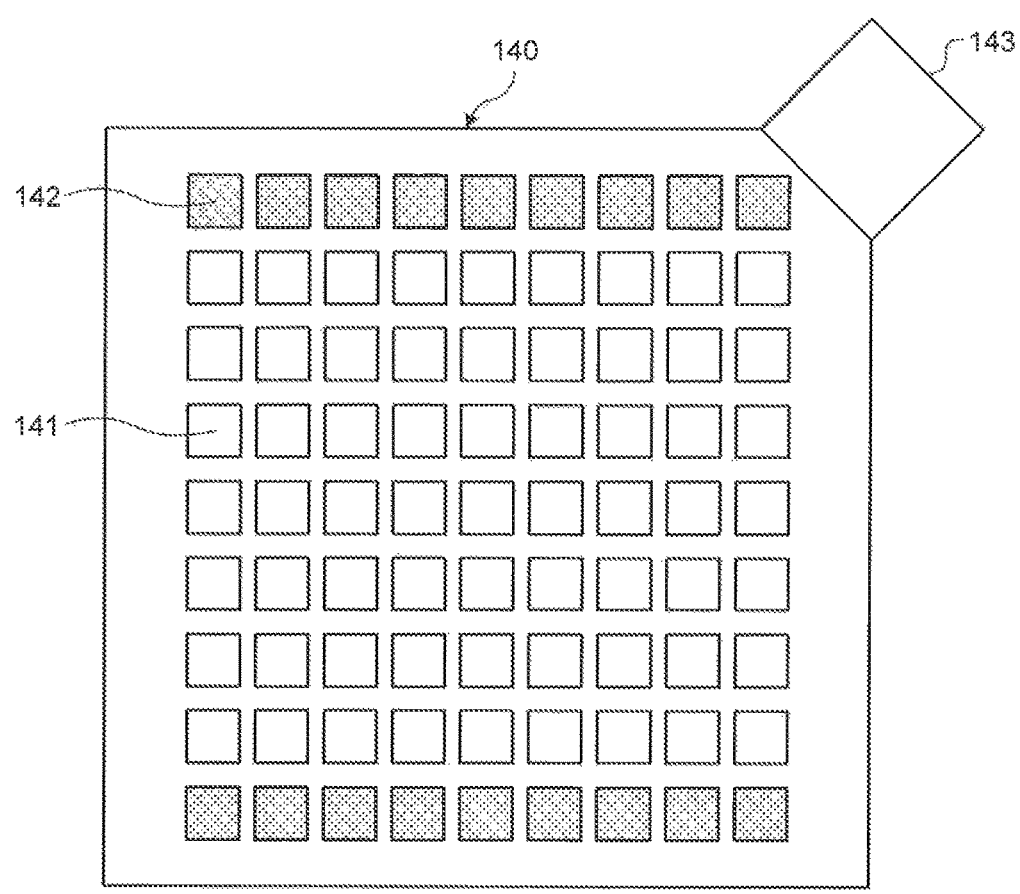
FIG. 6 is a diagram that schematically illustrates a first specific configuration example of the photon detecting element according to the embodiment.

Given below is the explanation of specific configuration examples of the photon detecting element 120 (or the photon detecting element 120a, or the photon detecting element 120b). FIG. 6 is a diagram that schematically illustrates a first specific configuration example of the photon detecting element 120 (or the photon detecting element 120a, or the photon detecting element 120b). As illustrated in FIG. 6, for example, the photon detecting element 120 is configured in such a way that a pixel 140 for detecting photons includes a plurality of first cells 141, a plurality of second cells 142, and through silicon via (TSV) 143.

For example, each first cell 141 includes a single APD 126, and detects photons. The output of each first cell 141 in the pixel 140 is connected to the TSV 143, which is in turn connected to, for example, the terminal 125 mentioned earlier. Moreover, the pulses that are output by each first cell 141 upon detecting photons are superimposed and are output as a pixel-by-pixel electrical current from the terminal 125 via the TSV 143. Thus, the number of first cells 141 in the pixel 140 is equivalent to the dynamic range per pixel.

The second cells 142 include, for example, the diode 122 (or a plurality of diodes 122a, or the Zener diode 122b) and are connected to the cathode of the APDs 126. For example, the diode 122 included in each second cell 142 is connected in a lump to the cathode of the APDs 126 of the first cells 141.

Figure 7:
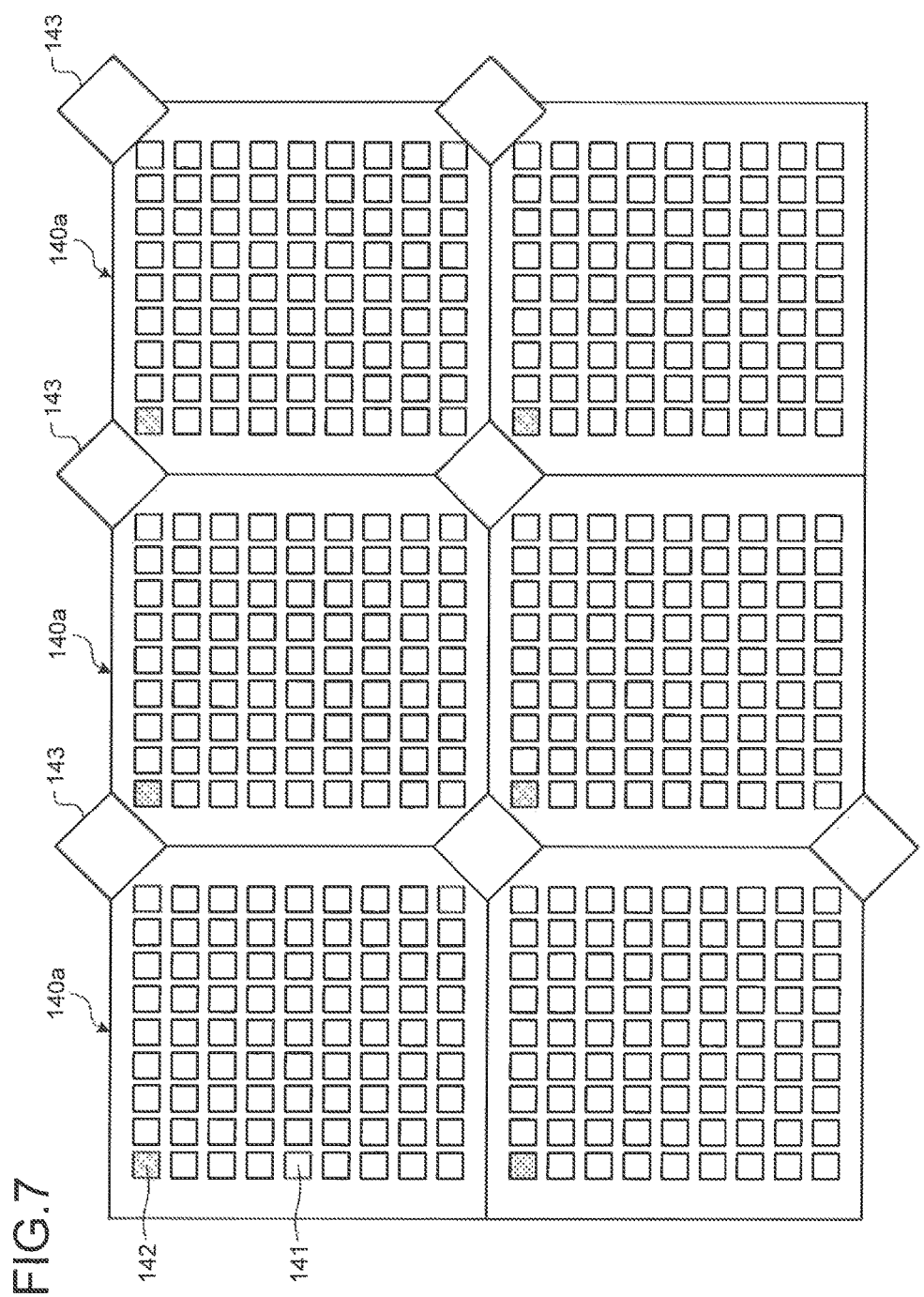
FIG. 7 is a diagram that schematically illustrates a second specific configuration example of the photon detecting element according to the embodiment.

FIG. 7 is a diagram that schematically illustrates a second specific configuration example of the photon detecting element 120 (or the photon detecting element 120a, or the photon detecting element 120b). As illustrated in FIG. 7, for example, the photon detecting element 120 includes a plurality of pixels 140a, each of which further includes a plurality of first cells 141, a single second cell 142, and the TSV 143. Meanwhile, of the constituent elements illustrated in FIG. 7, the constituent elements that are substantially identical to the constituent elements illustrated in FIG. 6 are referred to by the same reference numerals.

The second cell 142 is connected to the cathode of the APDs 126 in the corresponding pixel 140a. Alternatively, all second cells 142 can be connected in a lump to the cathode of the APDs 126 of all pixels 140a. That is, the photon detecting element 120 either can be configured to perform temperature compensation of the APDs 126 in the units of pixels or can be configured to perform temperature compensation of the APDs 126 in the units of chips.

In this way, the temperature coefficient (the first temperature coefficient) representing the variation of the breakdown voltage of the Zener diode 122b with respect to the temperature variation is substantially the same as the temperature coefficient (the second temperature coefficient) representing the variation of the breakdown voltage of the APDs 126 with respect to the temperature variation. Hence, the diode 122 (the nonlinear circuit) of the photon detecting element 120 can easily compensate for the temperature characteristic of the multiplication factor of the APDs 126. More particularly, in the photon detecting elements 120, 120a, and 120b; without having to install an external temperature measuring element and an external voltage control circuit, the temperature characteristic of the multiplication factor of the APDs 126 can be compensated with ease. Moreover, the compensation of the multiplication factor is done at high speeds because of the voltage control in the analog domain.

Illustrative Embodiment

Figure 8:
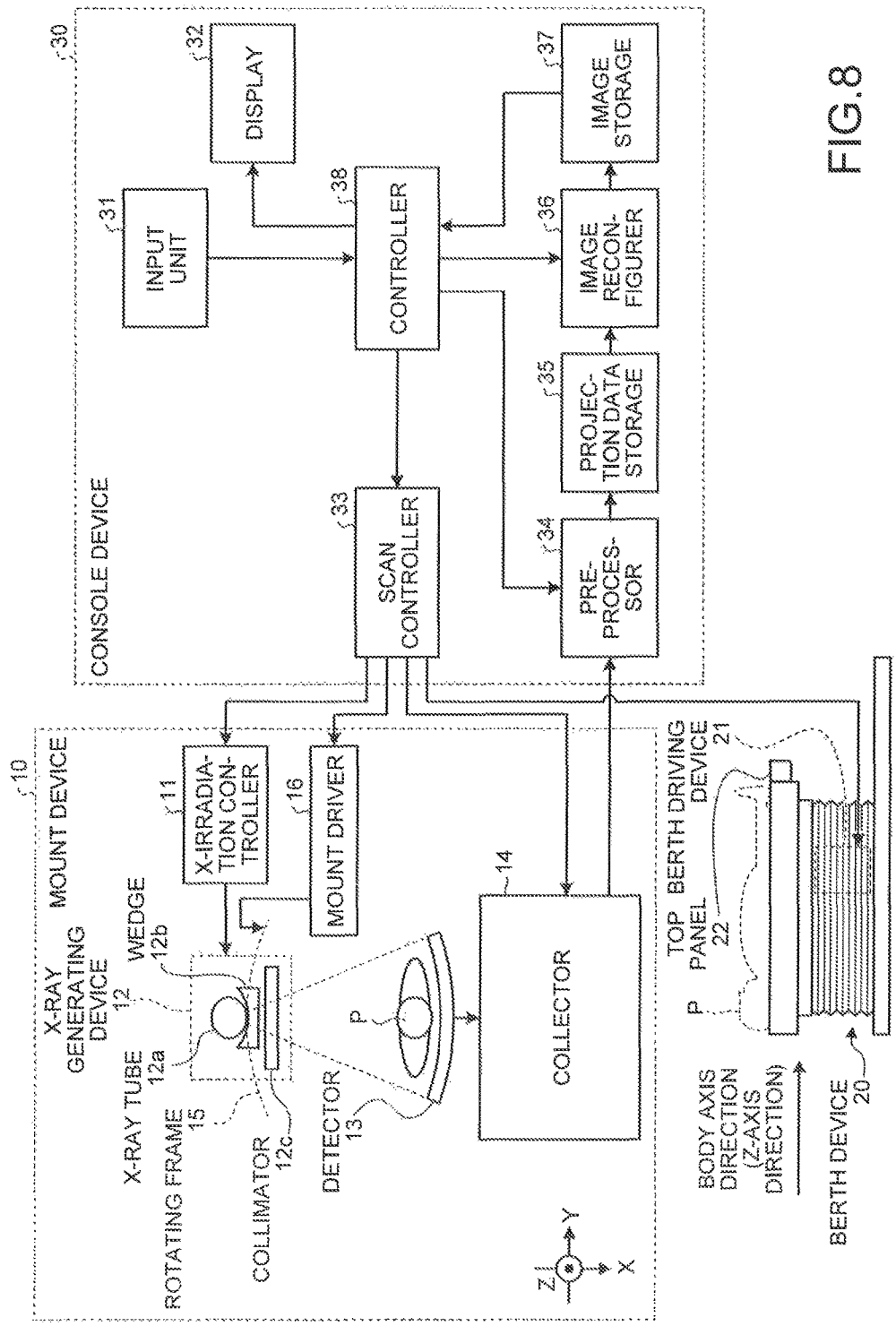
FIG. 8 is a configuration diagram illustrating an exemplary configuration of a radiation analyzing device according to the embodiment.
Figure 9:
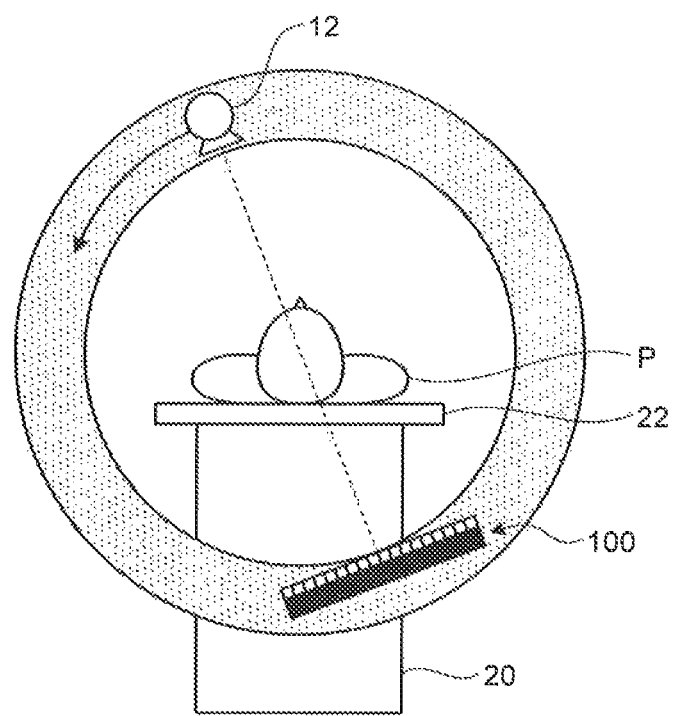
FIG. 9 is a schematic diagram that schematically illustrates the position of the photon detecting device in the radiation analyzing device.

Given below is the explanation of a radiation analyzing device that includes the photon detecting device 100 also functioning as a radiation detecting device. FIG. 8 is a configuration diagram illustrating an exemplary configuration of a radiation analyzing device that includes the photon detecting device 100. FIG. 9 is a schematic diagram that schematically illustrates the position of the photon detecting device 100 in the radiation analyzing device illustrated in FIG. 8. Herein, the radiation analyzing device is an X-ray computed tomography (CT) device that is capable of performing photon counting CT. That is, the radiation analyzing device includes the photon detecting device 100, and is thus capable of performing photon counting to count the photons attributed to the X-rays which have passed through a subject and accordingly reconfiguring X-ray CT image data having a high signal-to-noise (S/N) ratio.

Each individual photon has a different energy. During photon counting CT, if the energy values of the photons are measured, then it becomes possible to obtain information about the energy components of the X-rays. During photon counting CT, the data collected by means of X-irradiation at a single type of tube voltage can be divided into a plurality of energy components and an image thereof can be formed.

As illustrated in FIG. 8, the radiation analyzing device includes a mount device 10, a berth device 20, and a console device 30.

The mount device 10 is a device that bombards a subject P with X-rays and counts the X-rays that have passed through the subject P. The mount device 10 includes an X-irradiation controller 11, an X-ray generating device 12, a detector 13 (including the photon detecting device 100), a collector 14, a rotating frame 15, and a mount driver 16.

The rotating frame 15 is a ring-shaped supporting frame that supports the X-ray generating device 12 and the detector 13 in such a way that the X-ray generating device 12 and the detector 13 are positioned opposite to each other across the subject P. Moreover, the rotating frame 15 is rotated at high speeds in a circular path around the subject P by the mount driver 16 (described later).

The X-ray generating device (a radiation source) 12 is a device that generates X-rays and bombards the subject P with the X-rays. The X-ray generating device 12 includes an X-ray tube 12a, a wedge 12b, and a collimator 12c.

The X-ray tube 12a is a vacuum tube for bombarding the subject P with X-rays in response to a high voltage supplied from the X-irradiation controller 11 (described later). The X-ray tube 12a keeps rotating according to the rotation of the rotating frame 15 and bombards the subject P with X-ray beams. Meanwhile, the X-ray tube 12a generates X-ray beams that expand with a fan angle and a cone angle.

The wedge 12b is an X-ray filter used in adjusting the X-ray dosage of the X-rays bombarded from the X-ray tube 12a. More particularly, through the wedge 12b, the X-rays bombarded from the X-ray tube 12a pass and undergo attenuation in such a way that the X-rays bombarded toward the subject P have a predetermined distribution.

For example, the wedge 12b is a filter made by processing aluminum to have a predetermined target angle and a predetermined thickness. A wedge is also called a wedge filter or a bow-tie filter. Meanwhile, the radiation analyzing device includes a plurality of types of the wedge 12b that can be changed according to the imaging conditions. For example, the X-irradiation controller 11 (described later) switches between the types of the wedge 12b according to the imaging conditions. For example, the X-ray generating device 12 includes two types of the wedge 12b.

The collimator 12c is a slit that, under the control of the X-irradiation controller 11 (described later), narrows the range of bombardment of the X-rays for which the wedge 12b has adjusted the X-ray dosage.

The X-irradiation controller 11 functions as a high-voltage generating unit that supplies a high voltage to the X-ray tube 12a. Thus, the X-ray tube 12a generates X-rays using the high voltage supplied from the X-irradiation controller 11. Moreover, the X-irradiation controller 11 adjusts the tube voltage or the tube current supplied to the X-ray tube 12a and adjusts the X-ray dosage with which the subject P is bombarded.

Furthermore, the X-irradiation controller 11 switches between the types of the wedge 12b. Moreover, the X-irradiation controller 11 adjusts the aperture of the collimator 12c so as to adjust the range of bombardment (the fan angle or the cone angle) of the X-rays. Meanwhile, in the radiation analyzing device, switching between a plurality of types of wedges can be done manually by an operator.

The mount driver 16 rotary-drives the rotating frame 15 so that the X-ray generating device 12 and the detector 13 swirl on a circular path around the subject P.

The detector 13 includes the photon detecting device 100. Every time there is incoming radiation of X-ray photons, the detector 13 outputs signals that enable measuring the energy value of those X-ray photons. The photon detecting device 100 is so configured that a plurality of pixels 140 detects the photons generated by the X-rays falling on a fluorescent material (not illustrated). The X-ray photons referred to herein are, for example, the X-ray photons that are bombarded from the X-ray tube 12a and that have passed through the subject P. The radiation analyzing device can perform arithmetic processing and detect the energy value of the radiation detected by the photon detecting device 100.

The collector 14 (FIG. 8) collects counting information that represents the result of a counting operation performed using the output signals of the detector 13. That is, the collector 14 discriminates individual signals output from the detector 13 and collects the counting information. Herein, the counting information represents the information collected from individual signals that are output by the detector 13 every time the X-rays that are irradiated from the X-ray tube 12a and that have passed through the subject P fall on the detector 13. More particularly, the counting information represents the information in which the counted values and the energy values of the X-rays falling on the detector 13 are held in a corresponding manner. The collector 14 sends the collected counting information to the console device 30.

The berth device 20 is a device on which the subject P is made to lie down, and includes a top panel 22 and a berth driving device 21. The top panel 22 is a panel on which the subject is made to lie down. The berth driving device 21 moves the top panel 22 in the Z-axis direction so that the subject P moves inside the rotating frame 15.

The mount device 10 performs, for example, helical scanning in which the rotating frame 15 is rotated while moving the top panel 22 so that the subject P is scanned in a helical manner. Alternatively, the mount device 10 performs conventional scanning in which, after the top panel 22 is moved, the rotating frame 15 is rotated while keeping the position of the subject P fixed so that the subject P is scanned in a circular path. Still alternatively, the mount device 10 implements the step-and-shoot method in which the position of the top panel 22 is moved at regular intervals and the conventional scanning is performed at a plurality of scan areas.

The console device 30 receives operations performed by an operator with respect to the radiation analyzing device as well as reconfigures X-ray CT images using the counting information collected by the mount device 10. The console device 30 includes an input unit 31, a display 32, a scan controller 33, a preprocessor 34, a projection data storage 35, an image reconfigurer 36, an image storage 37, and a controller 38.

The input unit 31 includes a mouse or a keyboard that is used by the operator of the radiation analyzing device for the purpose of inputting various instructions and various settings; and transfers the instructions and the settings, which are received from the operator, to the controller 38. For example, from the operator, the input unit 31 receives imaging conditions related to X-ray CT image data, reconfiguration conditions at the time of reconfiguring the X-ray CT image data, and image processing conditions with respect to the X-ray CT image data.

The display 32 is a monitor device referred to by the operator. Under the control of the controller 38, the display 32 displays the X-ray CT image data as well as displays a graphic user interface (GUI) that enables the operator to input various instructions and various settings via the input unit 31.

The scan controller 33 controls the operations of the X-irradiation controller 11, the mount driver 16, the collector 14, and the berth driving device 21 under the control of the controller 38; and controls the counting information collecting operation in the mount device 10.

The preprocessor 34 generates projection data by performing correction operations such as logarithmic conversion, offset correction, sensitivity correction, and beam hardening correction with respect to the counting information sent from the collector 14.

The projection data storage 35 is used to store the projection data generated by the preprocessor 34. That is, the projection data storage 35 is used to store the projection data (i.e., the corrected counting information) that is used in reconfiguring the X-ray CT image data. In the following explanation, the projection data is sometimes written as counting information.

The image reconfigurer 36 reconfigures the X-ray CT image data using the projection data stored in the projection data storage 35. Herein, the reconfiguration can be performed by implementing various methods such as the back projection method. Examples of the back projection method include the filtered back projection (FBP). Moreover, the image reconfigurer 36 performs a variety of image processing with respect to the X-ray CT image data, and generates image data. Then, the image reconfigurer 36 stores, in the image storage 37, the reconfigured X-ray CT image data and the image data, which is generated by performing a variety of image processing.

The projection data that is generated from the counting information, which is obtained during photon counting CT, contains energy information of the X-rays that are attenuated due to passing through the subject P. Hence, for example, the image reconfigurer 36 can reconfigure the X-ray CT image data of particular energy components. Moreover, for example, the image reconfigurer 36 can reconfigure the X-ray CT image data of each of a plurality of energy components.

Furthermore, according to each energy component, the image reconfigurer 36 can assign a color tone to each pixel of the X-ray CT image data of that energy component; and can generate a plurality of sets of X-ray CT image data that is color coded according to the energy components. Moreover, the image reconfigurer 36 can generate image data by superposing these sets of X-ray CT image data.

Furthermore, the image reconfigurer 36 can make use of the matter-specific K adsorption end and generate image data that enables identification of the matter. Since the X-ray attenuation coefficient differs in a large way before and after the K adsorption end, the counted values also undergo a substantial change. For example, the image reconfigurer 36 generates difference image data, which represents the difference between image data in which the counting information of the energy area smaller than the K adsorption end is reconfigured and image data in which the counting information of the energy area greater than the K adsorption end is reconfigured. For example, difference image data generated using the K adsorption end of the principal component of a radiopaque dye represents an image mainly demonstrating the area in which the radiopaque dye is present. Meanwhile, examples of other types of image data generated by the image reconfigurer 36 include monochromatic X-ray image data, density image data, and effective-atomic-number image data.

The controller 38 controls the operations of the mount device 10, the berth device 20, and the console device 30; arid performs the overall control of the radiation analyzing device. More particularly, the controller 38 controls the scan controller 33 so as to control the CT scanning performed in the mount device 10. Moreover, the controller 38 controls the preprocessor 34 and the image reconfigurer 36 so as to control the image reconfiguration operation and the image generation operation performed in the console device 30. Furthermore, the controller 38 performs control to display a variety of image data, which is stored in the image storage 37, on the display 32.

Meanwhile, the photon detecting device 10 can also be used in devices other than the X-ray CT device described above. For example, the photon detecting device 100 can be used in a nuclear medicine imaging device such as an X-ray diagnostic apparatus, a positron emission computer tomography (PET) device, and a single photon emission computer tomography (SPECT) device. Similarly, the photon detecting device 100 can be used in a PET-CT device or a SPECT-CT device configured by integrating an X-ray CT device and a nuclear medicine imaging device. Moreover, the photon detecting device 100 can be used as a light receiving unit of a PET device so as to configure a device in combination with magnetic resonance imaging (MRI).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon detecting element comprising:
   one or more avalanche photodiodes, a temperature variation of breakdown voltage of the one or more avalanche photodiodes being a linear function of temperature; and
   a circuit configured to connect between cathodes of the one or more avalanche photodiodes and an external power source, and to compensate for the temperature variation of a breakdown voltage with a temperature variation of an electrical potential set at the cathodes thereby, wherein
   the circuit is driven in a constant current, the temperature variation of the set electrical potential is a linear function of temperature, and a first temperature coefficient of the temperature variation of the set electrical potential is substantially the same as a second temperature coefficient of the temperature variation of the breakdown voltage, thereby cancelling the temperature variation of the breakdown voltage by the temperature variation of the set electrical potential.

2. The photon detecting element according to claim 1, wherein the circuit includes one or more Zener diodes.

3. The photon detecting element according to claim 1, wherein the circuit includes one or more diodes to which forward voltage is applied.

4. A photon detecting device comprising:
   a power supply configured to apply to voltage to the cathodes via the circuit to operate the one or more avalanche photodiodes in Geiger mode;
   a current sink circuit configured to draw electrical current to make the power supply perform constant-current driving of the circuit; and
   the photon detecting element according to claim 1.

5. A radiation analyzing device comprising:
   a radiation source; and the photon detecting device according to claim 4 for detecting photons attributed to radiation emitted from the radiation source.

6. A radiation analyzing device comprising:

a radiation source; and a photon detecting device for detecting photons attributed to radiation emitted from the radiation source, the photon detecting device comprising:

one or more avalanche photodiodes, a temperature variation of a breakdown voltage of the one or more avalanche photodiodes being a linear function of temperature; and a circuit configured to connect between cathodes of the one or more avalanche photodiodes and an external power source, and to compensate for the temperature variation of the breakdown voltage with a temperature variation of an electrical potential set at the cathodes thereby, wherein the circuit is driven in a constant current, the temperature variation of the set electrical potential is a linear function of temperature, and a first temperature coefficient of the temperature variation of the set electrical potential is substantially the same as a second temperature coefficient of the temperature variation of the breakdown voltage, thereby cancelling the temperature variation of the breakdown voltage by the temperature variation of the set electrical potential.

* * * * *